United States Patent [19]

Kieslich et al.

[11] 4,247,635
[45] Jan. 27, 1981

[54] MICROBIOLOGICAL REDUCTION OF 15-KETOPROSTAGLANDIN INTERMEDIATES

[75] Inventors: Klaus Kieslich; Bernd Raduchel; Werner Skubalia; Helmut Vorbruggen; Helmut Dahl, all of Berlin, Fed. Rep. of Germany

[73] Assignee: Schering Aktiengesellschaft, Berlin and Bergkamen, Fed. Rep. of Germany

[21] Appl. No.: 100,571

[22] Filed: Dec. 5, 1979

[30] Foreign Application Priority Data

Dec. 8, 1978 [DE] Fed. Rep. of Germany ....... 2853637

[51] Int. Cl.³ ............................................. C12P 31/00
[52] U.S. Cl. .................................... 435/63; 435/911; 435/930; 435/941
[58] Field of Search ....................................... 435/63

[56] References Cited

U.S. PATENT DOCUMENTS

| 3,687,811 | 8/1972 | Colton et al. | 435/63 |
| 3,799,841 | 3/1974 | Marsheck et al. | 435/63 |

FOREIGN PATENT DOCUMENTS 1430191  3/1976  United Kingdom .

Primary Examiner—Lionel M. Shapiro
Attorney, Agent, or Firm—Millen & White

[57] ABSTRACT

A process for the preparation of a 15 α-hydroxyprostaglandin intermediate of the formula

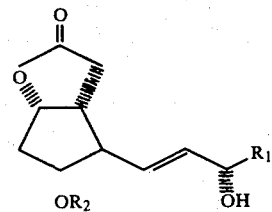

I, wherein
$R_1$ is phenoxymethyl, phenoxymethyl substituted on the phenyl moiety by halogen or trifluoromethyl, or alkyl of 1–5 carbon atoms, and
$R_2$ is hydrogen, acetyl, benzoyl or p-phenylbenzoyl, which comprises stereospecifically microbiologically reducing a corresponding 15-ketone of the formula

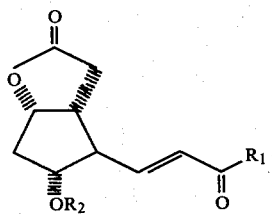

II, with a strain of the microorganism Kloeckera, Saccharomyces or Hansenula.

7 Claims, No Drawings

MICROBIOLOGICAL REDUCTION OF 15-KETOPROSTAGLANDIN INTERMEDIATES

BACKGROUND OF THE INVENTION

The present invention relates to a microbiological method for the stereoselective reduction of the 15-keto function in bicyclic prostaglandin intermediates to the corresponding 15-hydroxy compounds, viz., in such a manner that the resultant 15-hydroxy group, as well as an original 11-hydroxy group, are in the 6α-position.

Although the chemical reduction of 15-keto groups in prostaglandins and progstaglandin intermediates, for example with sodium borohydride, produces the desired 15α-hydroxyprostaglandins, it does so only by way of mixtures of the corresponding 15α- and 15β-hydroxy compounds and' only with the concomitant losses in yield which accompany the subsequent separating procedure thereby required. This problem has been somewhat alleviated by disclosure of a series of microorganisms (U.S. Pat. No. 3,687,811) which permit conversion of the 15-keto group in 11-hydroxy-15-oxo-prostaglandins to the corresponding trans-15-hydroxy group, its exact conformation depending on the original conformation of the 11-hydroxy group. Also, from DOS (German Unexamined Laid-Open Application) No. 2,357,815 or from the corresponding U.S. Pat. No. 3,799,841, there is known a microbiological method for converting, for example, an 11-hydroxy-15-oxoprostaglandin into a mixture of 11α, 15α- and 11β-, 15β-dihydroxyprostaglandins. This cis arrangement of the 11α, 15α-hydroxy groups is especially advantageous in that it corresponds to that of biologically active prostaglandins.

All these aforementioned processes, however, fail when applied to the microbiological reduction of (1S,5R,6R,7R)-6-[(E)-3-oxophenoxy-1-alkenyl]-7-hydroxy-2-oxabicyclo[3,3,0]octan-3-ones. Furthermore, the microbiological process described in DOS 2,401,761 or in the corresponding British Pat. No. 1 430 191 achieves only very low yields. In addition, this process has the disadvantage that the basidiomycetes employed for the reduction exhibit only a slow growth and cannot be handled readily since they are higher fungi.

SUMMARY OF THE INVENTION

Accordingly, it is an object of this invention to provide a process for stereoselectively reducing the 15-keto function of bicyclic prostaglandins without the foregoing disadvantages and with application to substrates which heretofore have not been able to be so reduced.

Upon further study of the specification and appended claims, further objects and advantages of this invention will become apparent to those skilled in the art.

These objects have been attained by this invention by providing a process for the preparation of a 15α-hydroxyprostaglandin intermediate of the formula

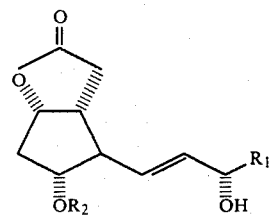

wherein
$R_1$ is phenoxymethyl, phenoxymethyl substituted on the phenyl moiety by halogen or trifluoromethyl, or alkyl of 1-5 carbon atoms, and
$R_2$ is hydrogen, acetyl, benzoyl or p-phenylbenzoyl, comprising stereospecifically, microbiologically reducing a corresponding 15-ketone of the formula

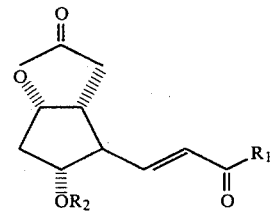

with a strain of the microorganism Kloeckera, Saccharomyces or Hansenula.

DETAILED DISCUSSION

The present invention is especially suitable for the microbiological reduction of the 3-oxo group in (1S,5R,6R,7R)-6-[(E)-3-oxophenoxy-1-alkenyl]-7-hydroxy-2-oxabicyclo[3,3,0]octan-3-ones to the (R)-3-hydroxy group with high yields. The process of this invention can also be advantageously applied to similar reduction of (1S,5R,6R,7R)-6-[(E)-3-oxo-1-alkenyl]-7-hydroxy-2-oxabicyclo[3,3,0]-octan-3-ones. Among the former 3-oxo compounds, the 3-oxo-4-phenoxy-1-butenyl compound is especially preferred for reduction via this invention.

Suitable strains of the aforementioned microbiological reduction agents include *Kloeckera magna* (ATCC 20 109), *Kloeckera jensenii* (ATCC 20 110), *Saccharomyces carlsbergensis* (CBS 1506), *Saccharomyces carlsbergensis* (CBS 1513) or *Hansenula anomala* (NRRL-Y-366). The strain *Kloeckera jensenii* (ATCC 20 110) has proven to be especially suitable.

Suitable halogens in Formula I include fluorine, chlorine and bromine, fluorine and chlorine being preferred.

If the phenyl ring in the phenoxymethyl residue of $R_1$ is substituted by halogen or trifluoromethyl, the 3- or 4-position is suitable for this purpose. The 3-position is preferred. Suitable substituted phenoxymethyl residues include: 3-chlorophenoxymethyl, 4-chlorophenoxymethyl, 3-fluorophenoxymethyl, 4-fluorophenoxymethyl, 3-trifluoromethylphenoxymethyl, 4-trifluoromethylphenoxymethyl and the like.

The $R_1$ $C_{1-5}$ alkyl groups may be straight-chained or branched, e.g., methyl, ethyl, n-propyl, isopropyl, n-butyl, sec-butyl, isobutyl, tert-butyl, n-pentyl, isopentyl, neopentyl, sec-pentyl, tert-pentyl, etc. Straight-chain alkyl groups of 3-5 carbon atoms are preferred.

The process works especially advantageously when $R_2$ in the compounds of Formula II is benzoyl or p-phenylbenzoyl. Depending on the $R_2$ moiety desired in the final product, the benzoyl or p-phenylbenzoyl blocking groups can be splitt-off according to conventional methods.

Among the various types of classes of microorganisms suitable for the reduction of this invention, differences are, of course, encountered regarding the effectiveness of each in the reduction of this invention. Good results have been attained with the mentioned specific strains, e.g., *Kloeckera magna* (ATCC 20 109), *Kloeckera jensenii* (ATCC 20 110), *Saccharomyces carlsbergensis* (CBS 1506), *Saccharomyces carlsbergensis* (CBS1513), and *Hansenula anomala* (NRRL-Y-366); reductions with the strain *Kloeckera jensenii* (ATCC 20 110) produce especially high yields.

To carry out the microbiological reduction conventional methodology is employed. Submerged cultures are incubated under the conventional culturing conditions for each of the aforementioned microorganisms, in a suitable nutrient medium with aeration, see also in Technic of Chemistry vol. 10, ser.ed. H. Weissberger—applications of biochemical systems in organic-chemistry, part 1 by J. B. Jones, C. H. J. Sih and D. Perlman,—J. Wiley, New York, 1976, pages 48–68. The substrate (dissolved in a suitable solvent or preferably in emulsified form) is then added to the culture, and the latter is fermented until maximum substrate conversion has been achieved.

Suitable substrate solvents include, for example, methanol, ethanol, glycol monometyl ether, dimethylformamide and dimethyl sulfoxide. The substrate can be emulsified, for example, by introducing the substrate in micronized form or dissolved in a water-miscible solvent (such as methanol, ethanol, acetone, glycol monomethyl ether, dimethylformamide or dimethyl sulfoxide) through nozzles under strong turbulence into (preferably demineralized) water containing conventional enulsifiers. Suitable emulsifying aids include nonionic emulsifiers, such as, for example, ethylene oxide adducts or fatty acid esters of polyglycols. Suitable emulsifiers include the commercially available surfactants "Tegin", "Tagat", "Tween" and "Span".

The emulsification of the substrates frequently causes increased throughput of the substrate and thus an increase in the substrate concentration. However, it is, of course, also possible to utilize in the process of this invention, other conventional methods for increasing the throughput of substrate, these being well-known to those skilled in the art of fermentation.

The optimum substrate concentration, the timing of the substrate addition, the duration of fermentation, etc. are dependent on the structure of the specific substrate employed and on the type of the microorganism utilized. These values are determined, as conventionally necessary in microbiological conversion reactions, in each individual case by preliminary routine experiments, readily performed by one skilled in the art. For a discussion of such microbiological reaction considerations, see for example K. Kieslich, Microbial transformation of nonsteroid cyclic compounds G. Thieme, Stuttgart, 1976, whose disclosure is incorporated by reference herein.

It is possible to produce pharmacologically active prostaglandins from the compounds of Formula I prepared by the process of this invention, using methods which maintain the center of asymmetry in the 15-position (prostaglandin nomenclature). For example, starting with (1S,5R,6R,7R)-6-[(E)-3-oxo-4-phenoxy-1-butenyl]-7-benzoyloxy-2-oxabicyclo[3,3,0]-octan-3-one, the following multistage synthesis yields the active agent "Sulproston" (described in DOS No. 2 355 540):

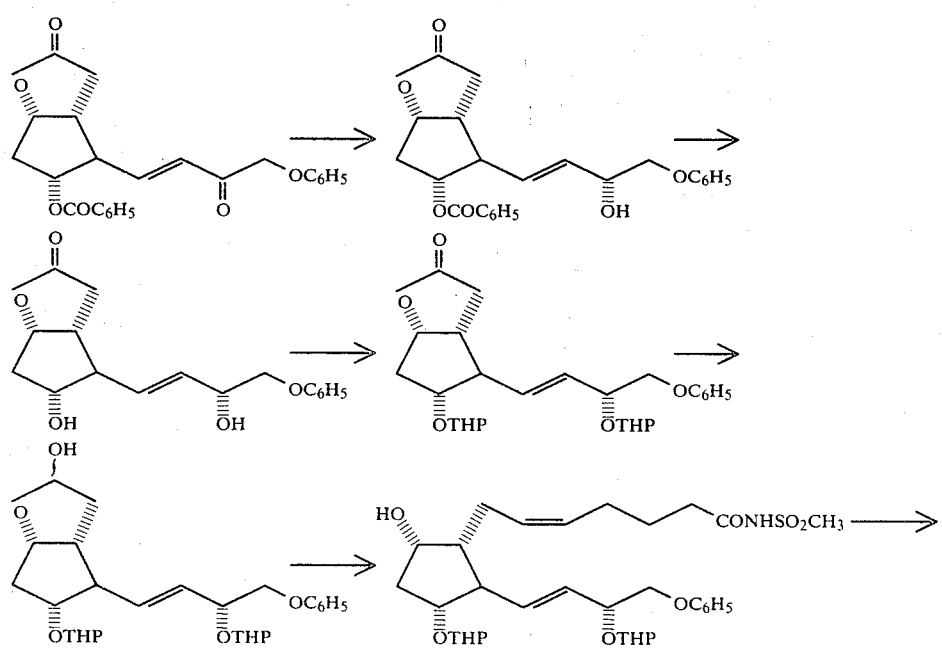

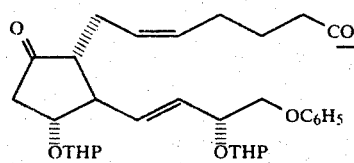 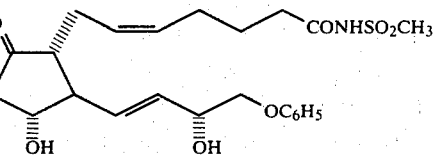

Other conventional methods can be used to prepare pharmacologically active prostaglandins from other 15-OH compounds prepared by this invention. See e.g., E. J. Corey et al. JACS 91 (1969), 5675 and 92 (1970), 397.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Erlenmeyer flasks having a capacity of 2 liters are charged with respectively 500 ml. of a nutrient solution made up of 5.0% glucose, 2.0% corn steep liquor, and are sterilized at 120° C. for 30 minutes in an autoclave. The flasks are inoculated with a supernatant broth of a 3-day-old tilted agar culture of *Kloeckera magna* (ATCC 20 109) and shaken for 48 hours on a rotary vibrator with a frequency of 145 r.p.m. at 30° C. Respectively 100 ml. of this preliminary culture serves for the inoculation of identically prepared flasks which are charged, after a shaking period of 6 hours, with solutions of respectively 125 mg. of (1S,5R,6R,7R)-6-[(E)-3-oxo-4-phenoxy-1-butenyl]-7-benzoyloxy-2-oxabicyclo[3,3,0]octan-3-one in 5 ml. of DMSO. By the removal of specimens at intervals for thin-layer analysis, the decrease in starting material is observed. At an extensively complete conversion, the mixture is extracted three times with respectively 200 ml. of methyl isobutyl ketone; the combined extracts are concentrated under vacuum; the residue is separated by column chromatography on silica gel with a gradient elution of hexane-methylene chloride. The (1S,5R,6R,7R,3'R)-6-[(E)-3-hydroxy-4-phenoxy-1-butenyl]-7-benzoyloxy-2-oxabicyclo[3,3,0]octan-3-one, obtained from the middle fractions, is recrystallized from a methylene chloride/hexane mixture.

Melting point: 129°/133°–134° C.

EXAMPLE 2

Under the conditions set forth in Example 1, the following strain is used for the desired keto reduction: *Saccharomyces carlsbergensis* CBS 1513.

EXAMPLE 3

*Saccharomyces carlsbergensis* CBS 1506.

EXAMPLE 4

*Hansenula anomala* (NRRL-Y-366).

EXAMPLE 5

*Kloeckera jensenii* (ATCC 20 110).

EXAMPLE 6

An Erlenmeyer flask having a capacity of 2 liters is charged with 500 ml. of a nutrient solution of 5.0% glucose and 2.0% corn steep liquor and sterilized in an autoclave at 120° C. for 30 minutes. The flask is inoculated with a supernatant broth of a 3-day-old tilted agar culture of *Kloeckera jensenii* (ATCC 20 110) and shaken for 48 hours on a rotary vibrator with a frequency of 145 r.p.m. at 30° C. A 20-liter fermentor, containing 15 l. of a sterilized medium of identical composition, is inoculated with 250 ml. of this preliminary culture, and the content is fermented after adding a few drops of defrother (polypropylene 2000) at 29° C. under aeration 1 volume of air per volume of fermentor broth per minute, and under agitation at 220 r.p.m. After an operating period of 24 hours, 900 ml. of the thus-obtained culture is transferred under sterile conditions into an identically prepared fermentor and fermented under the same conditions. After 12 hours, 10 g. of "Tween 80" is added thereto, and after 14 hours, a solution of 3.75 g. of (1S,5R,6R,7R)-6-[(E)-3-oxo-4-phenoxy-1-butenyl]-7-benzoyloxy-2-oxabicyclo[3,3,0]octan-3-one in 150 ml. of DMSO is added to the reaction mixture. After 12 hours of additional fermentation time, the culture broth is extracted three times with respectively 5 l. of methyl isobutyl ketone. The combined extracts are concentrated in a forced circulation vacuum evaporator at maximally 40° C. The crude product of this batch is chromatographed on silica gel and eluted with an ascending gradient system of hexane-methylene chloride (1:1) toward methylene chloride. After obtaining a forerun, the subsequent fractions contain the desired (1S,5R,6R,7R,3'R)-6-[(E)-3-hydroxy-4-phenoxy-1-butenyl]-7-benzoyloxy-2-oxabicyclo[3,3,0]octan-3-one; after recrystallization from carbon tetrachloride, 2.25 g. (60% of theory) of pure product is obtained.

Melting point: 129°/135°–136° C.

EXAMPLE 7

The fermentation is carried out under the same conditions as in Example 6 with *Hansenula anomala* (NRRL-Y-366), thus obtaining (1S,5R,6R,7R,3'R)-6-[(E)-3-hydroxy-4-phenoxy-1-butenyl]-7-benzoyloxy-2-oxabicyclo[3,3,0]octan-3-one.

Melting point: 120°/121°–122° C.

EXAMPLE 8

Under the conditions of Example 1, 125 mg. of (1S,5R,6R,7R)-6-[(E)-3-oxo-1-octenyl]-7-p-phenylbenzoyloxy-2-oxabicyclo[3,3,0]octan-3-one is fermented with a culture of *Kloeckera magna* (ATCC 20 109) for a contact period of 68 hours and then worked up. Chromatographic purification of the crude product yields an oil which is identical to the authentic material of E. Corey et al., J. Chem. Soc. 93: 1491 (1971).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a 15α-hydroxyprostaglandin intermediate of the formula

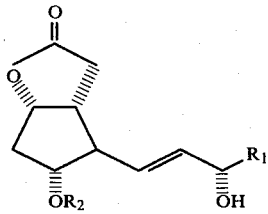

wherein

R₁ is phenoxymethyl, phenoxymethyl substituted on the phenyl moiety by halogen or trifluoromethyl, or alkyl of 1–5 carbon atoms, and R₂ is hydrogen, acetyl, benzoyl or p-phenylbenzoyl, comprising stereospecifically, microbiologically reducing a corresponding 15-ketone of the formula

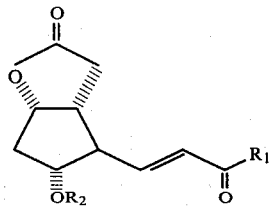

with a strain of the microorganism Kloeckera, Saccharomyces or Hansenula.

2. The process of claim 1, further comprising isolating the resultant 15α-hydroxyprostaglandin intermediate.

3. The process of claim 1, wherein the microorganism strain is *Kloeckera magna* (ATCC 20,109), *Kloeckera jensenii* (ATCC 20 110), *Saccharomyces carlsbergensis* (CBS 1506), *Saccharomyces carlsbergensis* (CBS 1513) or *Hansenula anomala* (NRRL-Y-366).

4. The process of claim 3, wherein the microorganism strain is *Kloeckera jensenii* (ATCC 20 110).

5. The process of claim 1 or 4, wherein the 15-keto starting compound is an (1S,5R,6R,7R)-6-[(E)-3-oxo-phenoxy-1-alkenyl]-7-hydroxy-2-oxabicyclo[3,3,0]octan-3-one.

6. The process of claim 1 or 4, wherein the 15-keto starting compound is (1S,5R,6R,7R)-6-[(E)-3-oxo-4-phenoxy-1-butenyl]-7-hydroxy-2-oxabicyclo[3,3,0]octan-3-one.

7. The process of claim 1 or 4, wherein the 15-keto starting compound is an (1S,5R,6R,7R)-6-[(E)-3-oxo-1-alkenyl]-7-hydroxy-2-oxabicyclo[3,3,0]octan-3-one.

* * * * *